(12) United States Patent
Hondroulis et al.

(10) Patent No.: US 9,068,180 B2
(45) Date of Patent: Jun. 30, 2015

(54) OIL ABSORPTION AND BIOREMEDIATION APPARATUS EMPLOYING OIL DIGESTING MICROORGANISMS

(71) Applicant: GEOPHIA LLC, Atlanta, GA (US)

(72) Inventors: Dimitros Hondroulis, Atlanta, GA (US); Troy W. Johnson, Atlanta, GA (US)

(73) Assignee: GEOPHIA LLC, Atlanta, GA (US)

( * ) Notice: Subject to any disclaimer, the term of this patent is extended or adjusted under 35 U.S.C. 154(b) by 0 days.

(21) Appl. No.: 13/947,470

(22) Filed: Jul. 22, 2013

(65) Prior Publication Data
US 2015/0024454 A1 Jan. 22, 2015

(51) Int. Cl.
*C12N 11/02* (2006.01)
(52) U.S. Cl.
CPC .................................... *C12N 11/02* (2013.01)

(58) Field of Classification Search
IPC ........................................................ C12N 11/02
See application file for complete search history.

(56) References Cited

U.S. PATENT DOCUMENTS

| | | |
|---|---|---|
| 5,958,182 A | 9/1999 | Hondroulis et al. |
| 6,027,652 A | 2/2000 | Hondroulis et al. |
| 6,506,307 B1 * | 1/2003 | Hondroulis et al. .......... 210/671 |

* cited by examiner

*Primary Examiner* — Rosanne Kosson
(74) *Attorney, Agent, or Firm* — Nelson Mullins Riley & Scarborough LLP

(57) ABSTRACT

An absorbent material may include banana tree stalk fibers separated and processed for moisture content reduction to generate processed fibers, and oil eating microorganisms (OEMs) infused into the processed fibers to form OEM infused fibers. The processed fibers may be configured to concentrate oil therein responsive to exposure to the oil. The OEMs may remain in a dormant state in the OEM infused fibers until activated by water and exposed to the oil.

6 Claims, 4 Drawing Sheets

OIL ABSORPTION AND BIOREMEDIATION APPARATUS EMPLOYING OIL DIGESTING MICROORGANISMS

TECHNICAL FIELD

Example embodiments generally relate to oil cleanup technology, and more specifically relate to the use of microorganisms that digest oil in an apparatus employing banana fibers.

BACKGROUND

There are a number of tropical plants that produce fruit or other useful foodstuffs. These types of plants are popular for harvesting, and thus cultivation of such plants is common. However, with the exception of the fruit itself, the majority of the material associated with harvesting the fruit of these plants is generally considered to be waste material. Accordingly, the fibrous stalks of such plants are often disposed of in landfills or in other manners that are either not beneficial for the environment or, in some cases, may actually harm the environment. Although some of the discarded plant matter may be used as natural fertilizer, there may be still more uses for the fibrous stalks of some such plants.

Banana stalks are one example of a tropical plant that has a fibrous stalk that is often wasted. In this regard, the banana stalk dies after the fruit is produced and harvested, and it is common for the stalks, which are typically cut off to harvest the bananas, to be thrown away. These fibrous stalks of the banana tree and some other tropical plants can have greater than 90% of their weight comprised of water and natural latex content that may include a variety of resinous and gummy substances. Accordingly, in order to produce workable or useable fibers, the fibrous material must be cleaned and processed. In particular, much of the fluid within the stalks must be removed, and the latex or other natural resinous substances must also be extracted or washed out.

After cleaning and processing, the fibers produced from the stalks may be incorporated into various useful products. However, by simple and direct incorporation of the fibers into certain products without additional modification, some of the potential uses of the fibers may not be optimized.

BRIEF SUMMARY OF THE INVENTION

Accordingly, some example embodiments may enable the provision of oil digesting microorganisms (e.g., microbes, bacteria, and/or the like) into the fibers of an absorbent apparatus formed from processed banana fiber. The oil digesting microorganisms may remain dormant within the absorbent apparatus until certain conditions are encountered, at which time the microorganisms may be triggered into action to digest petroleum products in the absorbent apparatus. After the petroleum products have been digested, the microorganisms may transition back to a dormant state until another food source is encountered.

In one example embodiment, an absorbent material is provided. The absorbent material may include banana tree stalk fibers separated and processed for moisture content reduction to generate processed fibers, and oil eating microorganisms (OEMs) infused into the processed fibers to form OEM infused fibers. The processed fibers may be configured to concentrate oil therein increasing the OEM's exposure to the oil. The OEMs may remain in a dormant state in the OEM infused fibers until activated by water and exposed to the oil.

In another example embodiment, a process for producing absorbent materials is provided. The process may include reducing a banana tree stalk into separated fibers, processing the separated fibers to reduce moisture content thereof to generate processed fibers, infusing oil eating microorganisms (OEMs) into the processed fibers to create OEM infused fibers, and incorporating the OEM infused fibers into an absorbent material.

In another example embodiment, a system for producing absorbent materials is provided. The system may include a reducer configured to reduce a banana tree stalk into separated fibers, a processing assembly configured to process the separated fibers to reduce moisture content thereof to generate processed fibers, and an oil eating microorganisms (OEMs) infusion assembly configured to infuse OEMs into the processed fibers to create OEM infused fibers for incorporation of the OEM infused fibers into an absorbent material.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
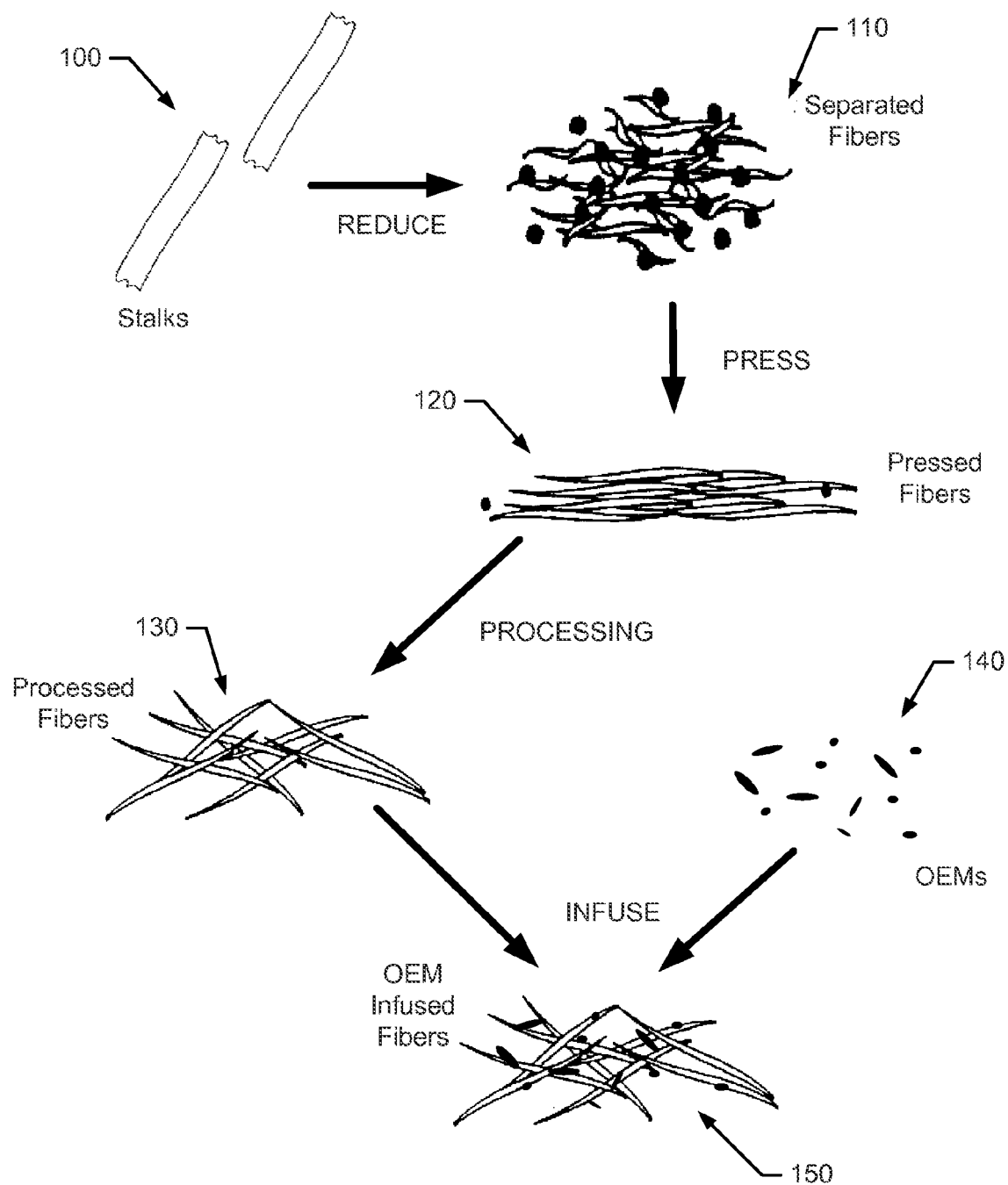
FIG. 1 illustrates a diagram of the states of materials associated with a process for producing absorbent materials according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

It should be appreciated that although an example embodiment is described below in the context of banana stalks, alternative embodiments may also be practiced in connection with other tropical plants. Thus, the specific example described herein should be regarded as non-limiting with regard to the specific materials used. As such, banana stalks or other tropical plant materials that are naturally hydrophobic, but may be processed as described herein to generate improved or optimal hydrocarbon absorption and digestion properties should be regarded as candidates for use in connection with the processes and materials described herein.

Some example embodiments may enable the provision of a process for converting the stalks of a banana tree that bears fruit into a plurality of fibers that are optimal for use in the absorption of hydrocarbons. These fibers may then be further processed to incorporate microorganisms (e.g., microbes, bacteria, and/or the like) that digest oil or other petroleum products. The microorganisms may remain dormant within the fibers until triggered to activate in the presence of water and absorbed petroleum products. The absorbed petroleum products may therefore be digested by the oil-digesting microorganisms (or oil eating microorganisms (OEM)) and go dormant again after the oil digestion is complete. As such, a reusable and environmentally friendly absorbent apparatus or material may be provided that can facilitate cleanup of oil spills or other such hazards.

OEMs may come in a number of different forms. Alcanivorax Borkumensis, *Cycloclasticus*, Colwellia, Oceanospirillales, Oleispira, Neptunomonas, *Thalassolituus Oleivorans, Pseudomonas*, Archaea and other oleophilic microorganisms are just a few examples of OEMs that could be employed in some embodiments. Family members of these OEMs or even other OEMs may alternatively be employed in some embodiments. The OEMs may be useful in the context of environmental bioremediation by absorbing, neutralizing, destroying or otherwise rendering oil or other petroleum products harmless by decreasing them to acceptable levels or eliminating them completely within a given environment.

Petroleum products such as oil are comprised of hydrocarbons. OEMs consume hydrocarbons and occur naturally in our oceans and even on land. In many cases, these OEMs remain dormant, or exist at very low levels, until they encounter significant quantities of oil. At that time, the OEMs may experience a "bloom" or rapidly multiply in the presence of an increased quantity of food (i.e., the oil). The presence of a plentiful food source supports the bloom until the amount of food consumed is too great to support further growth of OEM populations. As the quantity of oil decreases, the OEM population also decreases until, when the food source is virtually eliminated, the OEM population that remains may go dormant again.

The OEMs typically break down the petroleum products to molecule level, thereby increasing the surface area of the petroleum products. Oxygenation processes may be enhanced by the increase in surface area. The oxygenation process may be a trigger for revival or activation of dormant OEMs. Once revived, the activated OEMS begin feeding on the hydrocarbons in the petroleum products. The feeding process breaks the hydrocarbons down into fatty acids or carboxylic acid. The fatty acids or carboxylic acid may then be broken down into energy and carbon atoms to generate energy as part of a citric acid cycle. As a result, basic, non-toxic elements are generated from the digestion process including carbon, carbon dioxide, base elements and water.

According to an example embodiment, hydrophobic fibers that are processed to enhance their oil absorptive characteristics may have the OEMs attached thereto. The OEMs may therefore remain dormant within the fibers until a triggering event occurs. The triggering event may be the deployment of a material or apparatus having the fibers with dormant OEMs therein into a petroleum product in an aqueous environment. For example, the material or apparatus may be placed into an oil spill on the ground or in water or some other substance. The oil may be absorbed into the material or apparatus and the OEMs may be activated by water to digest the oil that is absorbed.

In some cases, the OEMs are activated by water and may be triggered in the presence of oil, but may also prosper in certain environmental conditions (e.g., certain temperature ranges, pH ranges, salinity ranges, etc.). In such situations, the environmental conditions may also form or further facilitate activation of triggering mechanisms. Thus, it may be possible to select specific strains of OEMs to be provided into the fibers of absorbent materials in order to optimize the absorbent materials for use in specific situations. Moreover, the absorbent materials may be provided into any desirable form factor (e.g., wipes, rags, towels, pillows, booms, loose absorbent materials, and/or the like) for deployment in environments that are expected to be encountered in the respective specific situations.

FIG. 1 illustrates a diagram of the states of materials associated with the provision of an oil absorption and bioremediation apparatus prepared in accordance with an example embodiment. In this regard, the diagram of FIG. 1 shows one example process for reduction of the banana tree stalk into separated fibers that can then be processed in a manner that accentuates their absorptive capabilities relative to absorption of petroleum products and also renders them capable of hosting OEMs. The result is a microbe infused fiber (MIF) that forms a natural, sustainable product comprised of banana fiber infused with microorganisms that digest and remediate oil in aquatic, marine and terrestrial environments. It should be appreciated that other processes may be used for the preparation of the separated fibers, however. Thus, the process shown in FIG. 1 is merely exemplary.

As shown in FIG. 1, banana stalks 100 may be employed in connection with some embodiments. The banana stalks 100 may be obtained, for example, after fruit has been removed from the stalks, leaving the banana stalks 100 as a byproduct of the harvesting process. The banana stalks 100 may then be reduced into separated fibers 110. The separated fibers 110 may then be pressed to generate pressed fibers 120 that have a relatively high percentage of the excess natural resinous substances removed therefrom. In this regard, for example, water, latex and other natural juices within the fibers may be removed while forming the pressed fibers 120. The pressed fibers 120 may then be processed to generate processed fibers 130. The processed fibers 130 may be washed, pre-dried, dried and/or exposed to any number of other processing operations to reduce the moisture levels of the fibers and produce the processed fibers 130.

The processed fibers 130 may be infused with OEMs 140 to provide OEM infused fibers 150. The OEM infused fibers 150 may include OEMs that are dormant until they are activated by water and encounter a food source (e.g., petroleum products). The OEM infused fibers 150 may then be used to make paper, loose absorbent materials or other sorbent materials. In particular, the OEM infused fibers 150 of some example embodiments may be employed within materials that are to be used for absorption of hydrocarbons such as petroleum products and the like so that the petroleum products can be digested by the OEMs.

Figure 2:
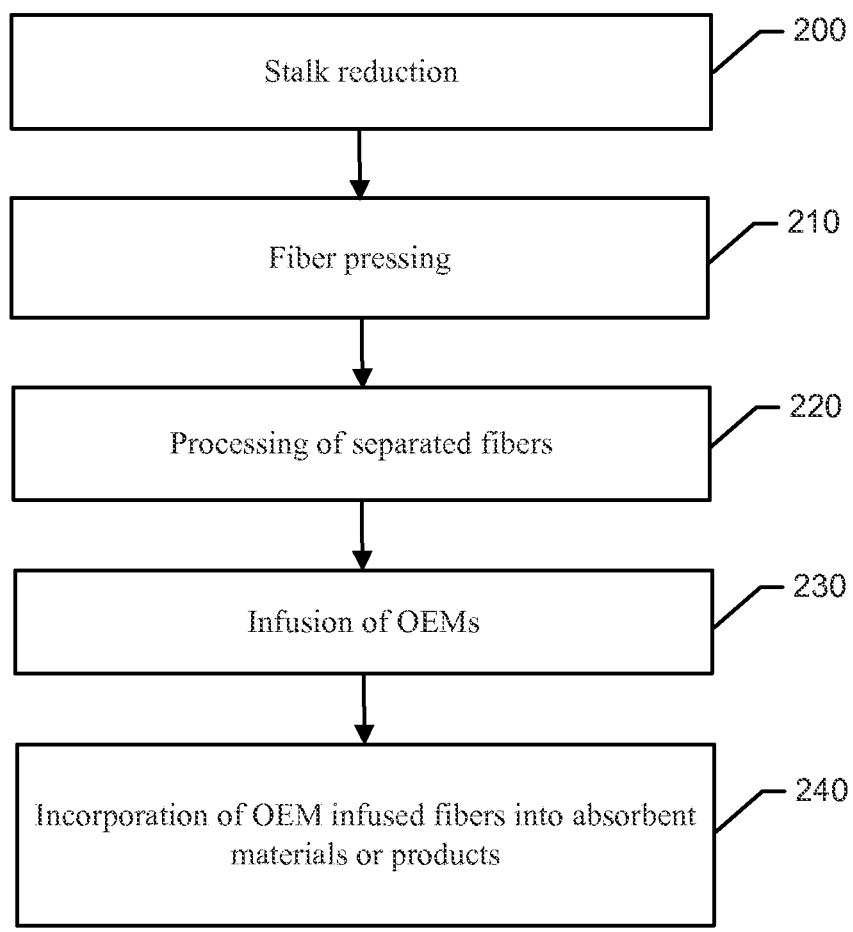
FIG. 2 illustrates a block diagram of a method for producing absorbent materials according to an example embodiment.
Figure 3:
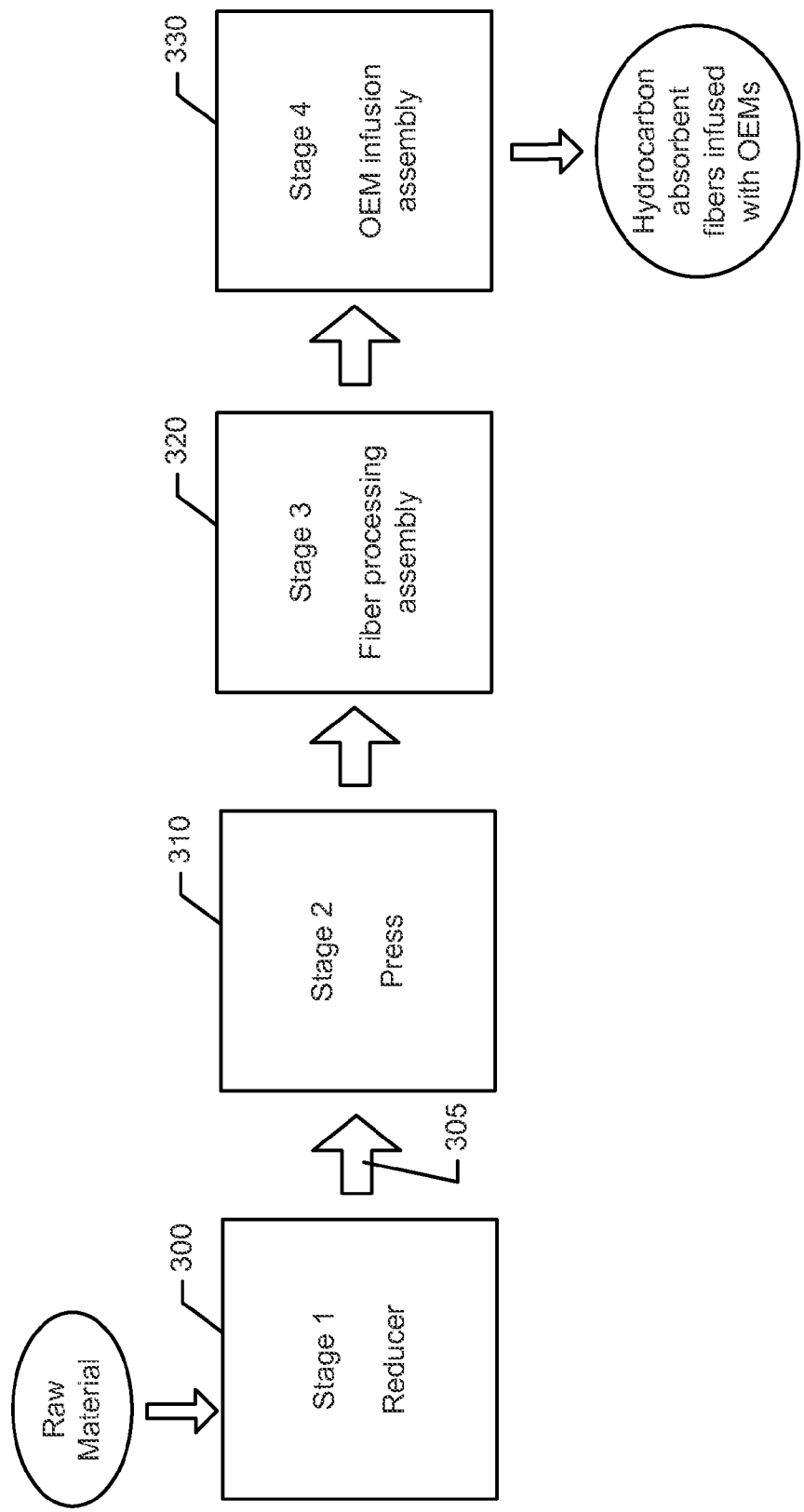
FIG. 3 illustrates a block diagram representing the equipment and corresponding processing stages associated with the method for producing absorbent materials in accordance with an example embodiment.

FIG. 2 illustrates a block diagram of a method of processing the material through the states shown in FIG. 1. FIG. 3 illustrates a block diagram showing the equipment that may be involved in each stage or operation of the process of FIG. 2 according to one example embodiment. An example embodiment will now be described in reference to FIGS. 1 to 3. In this regard, as shown in FIG. 2, the banana tree stalks 100 may be the raw material that is initially reduced (e.g., to form the separated fibers 110) at operation 200. Stalk reduction may include any or all of the operations of cutting the stalks and grinding, shredding or otherwise processing the stalks to separate the fibers therein. The separated fibers are naturally hydrophobic, but may readily absorb oils or other petroleum products.

The stalk reduction of operation 200 may be performed as a first stage process in a reducer 300. The reducer 300 may include a bladed roller that draws the banana tree stalks 100 into a series of rotating knives or blades. The rotating knives or blades may then cut the stalks into pieces that may have any desirable length while separating the fibers. The fibers may then be propelled through a grinder neck before being passed along to a press 310. Although the separated fibers 110 could be washed at this stage, an example embodiment may be practiced without washing the separated fibers 110 in order to reduce the cost, energy consumption and time of processing.

At operation 210, the separated fibers 110 may be pressed in the press 310 for second stage processing. The press 310 may be a hydraulically operated press, screw press, belt press, or any other suitable pressing device. In an example embodiment, pressing of the separated fibers 110 at operation 210 may remove a high percentage of excess natural resinous substances (e.g., latex), water, juice and/or other liquids from the separated fibers 110 to produce the pressed fibers 120, which may have a water and natural liquid content of about 43% to about 48% by weight. Thus, a reduction from greater than 90% moisture content by weight to about ½ that amount may be achieved via the press 310. The pressing operation may remove the naturally resinous substances (e.g., latex) in a manner that opens the natural capillaries in the fiber when the latex and other fluids are extracted. The open capillaries may be more receptive to hydrocarbon absorption and therefore may facilitate the ultimate production of materials that are highly absorbent of hydrocarbons, and are capable of concentrating oil or other petroleum products therein.

In an example embodiment, the separated fibers 110 may be transferred to the press 310 from the reducer 300 by hand or by a conveyor device 305 that extends between the reducer 300 and the press 310. Similarly, the pressed fibers 120 from the press 310 may be transported to or between each of the subsequent stages by a conveyor device or by hand. In some cases, the conveyor device may incorporate agitation paddles or other means by which to further separate or aerate fibers and to facilitate drying both while the fibers are transported and when the fibers undergo further processing.

In some embodiments, the third stage processing may include processing of separated fibers at operation 220 by a fiber processing assembly 320. The processing of separated fibers 110 may include any one or more of sub-processes including washing, treating, pre-drying and drying processes that may dry the separated fibers to prepare them for infusion with OEMs. The order of the sub-processes employed in the fiber processing of operation 220 may vary in different example embodiments, and the specific activities involved in execution of each of the sub-processes may also vary. Although not required, in some cases, the processing of operation 220 may include washing of fibers to facilitate removal of latex and/or fluids in the pressed fibers 120. The washing may be accomplished using water alone, or may further include the addition of a solution including potassium hydroxide, hydrogen peroxide, sodium hydroxide or the like. Thus, for example, the processing of operation 220 may a include treatment with solutions or fluids aimed at cleaning the fibers and/or enhancing certain characteristics of the fibers. In some cases, the processing of operation 220 may include passing the pressed fibers 120 through one or more heating processes that may facilitate drying of the pressed fibers 120 (e.g., from about 45% moisture content to about less than 30% moisture content). The heating processes may include passage of the fibers proximate to an infrared or other heating device. The heating device may include a conveyor that passes the pressed fibers 120 under a halogen lamp or other heat generation means. The speed of the conveyor and the distance between the halogen lamp (or lamps) and the pressed fibers 120 in this stage may be configured to achieve the desired amount of moisture removal within a corresponding desired amount of time.

In some embodiments, the processing of operation 220 may include drying of the pressed fibers 120 using one or more of heat, airflow and kinetic energy. In some cases, the drying performed in connection with operation 220 may include the use of a non-thermal dryer. In an example embodiment, the non-thermal dryer may be configured to perform agitation or grinding of material while simultaneously drying the material using airflow. Thus, no heat input is required while grinding and drying are simultaneously accomplished in a one-step process. In some embodiments, the non-thermal dryer may employ non-thermal, kinetic disintegration, pulverization that may be provided, for example, by a kinetic disintegration system (KDS). As such, in some embodiments, the non-thermal dryer may be embodied as a non-thermal, kinetic disintegration, pulverization device configured to lower moisture content of the fibers to less than 10% by weight.

The processed fibers 130 that result from the processing of operation 220 may thereafter be infused with OEMs 140 at operation 230 by an OEM infusion assembly 330. The OEM infusion assembly 330 may be configured to introduce OEMs 140 to the processed fibers 130 by any suitable mechanism. The OEMs 140 may be infused into the banana fibers of the processed fibers 130 and become resident in the fibers in a dormant state to generate the OEM infused fibers 150. Thereafter, at operation 240, the OEM infused fibers may be incorporated into absorbent materials or products such as loose fiber absorbents, booms, pillows, rags, wipes and/or the like.

In some embodiments, the OEMs 140 may be infused in and between fibers when the fibers are amassed for incorporation into other materials. However, it may also be possible to incorporate solutions or other materials that facilitate adhesion between the OEMs 140 and the fibers during the infusion process. Regardless of the mechanism by which the OEMs 140 are infused into the fibers to generate the OEM infused fibers 150, the resulting material includes dormant populations of OEMs 140 within banana fibers that may be incorporated with or without other fibers or materials into any of the absorbent apparatuses or materials described above or other compounds. The OEM infused fibers 150, and the apparatuses and materials into which they are incorporated, may then be employed to absorb oil or other petroleum products.

In some embodiments, the infusion of the OEMs 140 with the fibers may occur prior to the incorporation of the fibers into an absorbent material. Thus, for example, when loose fiber absorbents, booms, pillows, rags, wipes and/or the like are produced, the fibers therein may be infused with OEMs 140 during or prior to the production of such materials. However, in other example embodiments, the infusion may occur in-situ. In other words, the infusion may happen with absorbent materials and microbes that are initially kept apart, but are combined at the time of deployment. As one example, an absorbent boom may be provided with banana fibers processed as described above except that the infusion step is not complete. A separate container of microbes may be provided in a "side-by-side" fashion so that the infusion can be accomplished by combining the microbes in a water-soluble container with the boom during deployment. As such, infusion may be accomplished prior to or during deployment in various example embodiments.

Figure 4:
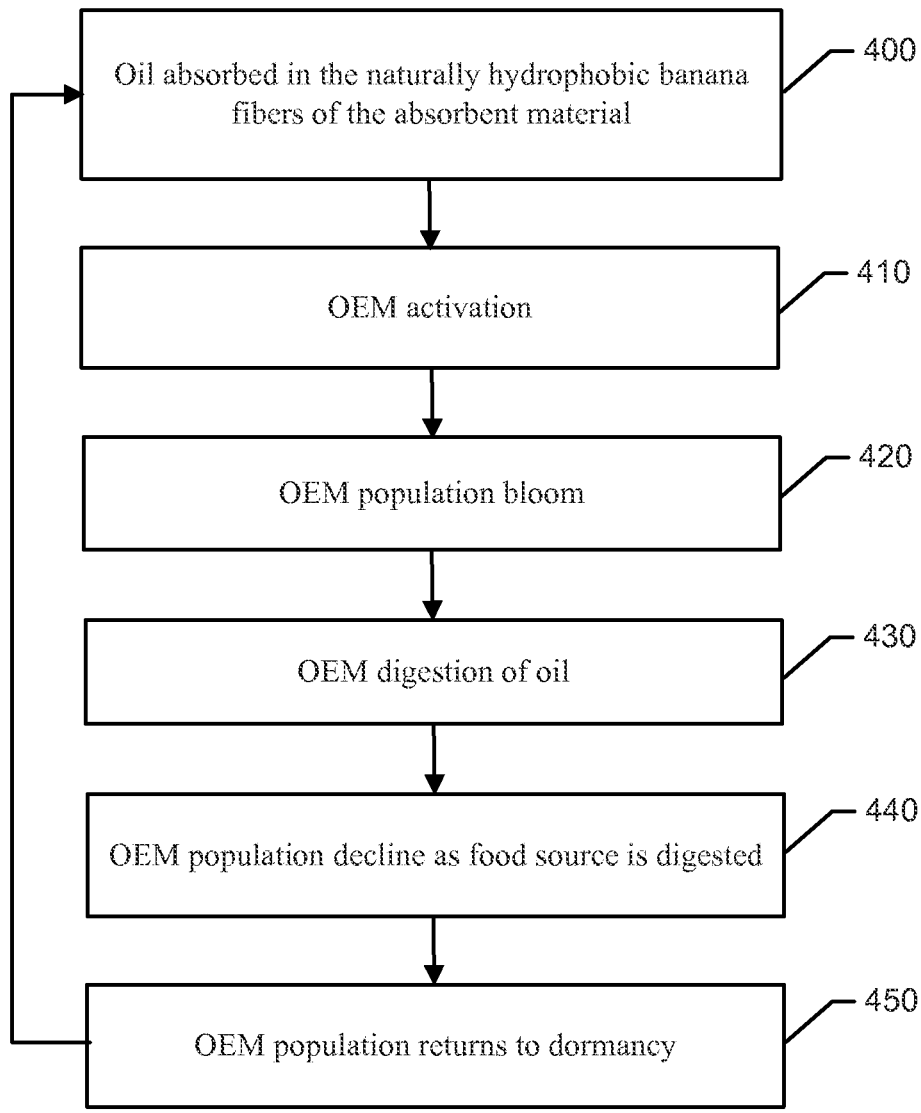
FIG. 4 illustrates a block diagram of the usage cycle of an absorbent material or product created using absorbent fibers infused with OEMs in accordance with an example embodiment.

FIG. 4 illustrates a block diagram of the usage cycle (e.g., and exposure and exhaustion cycle) of an absorbent material or product created using hydrocarbon absorbent fibers infused with OEMs in accordance with an example embodiment. In this regard, at operation 400, oil or other petroleum products are absorbed in the naturally hydrophobic banana fibers of the absorbent material (e.g., loose absorbent material, wipes, rags, towels, pillows, booms and/or the like). This may occur responsive to placement of the absorbent material onto the surface of an aquatic or marine environment (e.g., to absorb oil on the surface responsive to a spill generating an oil slick), or responsive to placement of the absorbent material onto a terrestrial surface. Thus, the absorbent material may float, or simply sit on a terrestrial surface.

At operation 410, the OEMs infused within the absorbent material may be activated and the OEM populations may begin to expand while the oil or other petroleum products are available as a source of food to the resident as well as introduced populations at operation 420. The OEMs may then digest the oil or other petroleum products as described above at operation 430. Of note, operations 420 and 430 may temporally overlap and occur simultaneously. As the food source is consumed due to digestion of the oil or other petroleum products, the population of the OEMs may begin to decline at operation 440. Finally, when the food source is removed due to digestion of all of the oil or other petroleum products absorbed in the absorbent material, the remaining OEMs return to dormancy at operation 450.

Thereafter, the absorbent material is available for reuse, returning to operation 400 for a repeat of the cycle. However, it should also be appreciated that the material can be cycled back to operation 400 at any time during the cycle, or may continuously remain within an oily environment indefinitely, during which time the cycle may remain at operation 430.

The OEM infused absorbent materials (i.e., MIF) of example embodiments may not have any salinity or pH altering components, and may not include outside chemical agents such as dispersants. Accordingly, the MIF of example embodiments may form an organic, all natural product that may cause no negative impacts to aquatic, marine or terrestrial ecosystems by virtue of its constituent parts. Moreover, the MIF may absorb oil or other petroleum products and concentrate the same within its hydrophobic banana fibers so that OEMs attached to the MIF may digest the oil and break it down into constituent parts such as carbon, carbon dioxide, base elements and water that are either environmentally benign or may form natural food sources for other indigenous life. By absorbing the oil within the MIF, the unique microstructure of individual banana fibers that are hydrophobic, but absorptive of oil (oleophilic), the oil can be concentrated as a food source for the OEMs. The OEMs are therefore kept dormant until activated by water and exposed to a food source and then given direct access to the food source when oil is absorbed in the MIF. Accordingly, the activation by water may be performed concurrently with exposure to the food source, or prior to the exposure to the food source. As the oil source is consumed, the food source is diminished and OEM populations decrease down to pre-spill levels. The OEMs then return to dormancy until a new food source (i.e., another spill) is presented, and the cycle may begin again.

Thus, according to an example embodiment, a process for producing absorbent materials is also provided. The process may include reducing a banana tree stalk into separated fibers, processing the separated fibers to reduce moisture content thereof to generate processed fibers, infusing oil eating microorganisms (OEMs) into the processed fibers to create OEM infused fibers, and incorporating the OEM infused fibers into an absorbent material. A corresponding system is also provided including various pieces of equipment that are employed to carry out the process.

In an example embodiment, the operations of the process described above may be modified, augmented or supplemented with additional optional operations. Some examples of such modifications, augmentations or supplementations are described below. The modifications, augmentations or supplementations may be employed either alone or in any combination with each other. In an example embodiment, processing the separated fibers may include pressing the separated fibers using a hydraulic press, a screw press or a belt press to remove water, latex, or natural juices. In some cases, processing the separated fibers includes one or more of washing, treating, pre-drying and drying the separated fibers. In some embodiments, drying the separated fibers employs one or more of heat, airflow and kinetic energy application methods. In an example embodiment, infusing the OEMs may include infusing OEMs that remain in a dormant state in the OEM infused fibers until activated by water and exposure to a petroleum product occurs. In some cases, incorporating the OEM infused fibers into the absorbent material may include incorporating the OEM infused fibers into one or more of a loose absorbent material, a wipe, a rag, a towel, a pillow or a boom. In an example embodiment, the processed fibers concentrate the petroleum product and the OEMs digest the petroleum product and return to dormancy when the petroleum product is exhausted.

An absorbent material is also provided that may include banana tree stalk fibers separated and processed for moisture content reduction to generate processed fibers, and oil eating microorganisms (OEMs) infused into the processed fibers to form OEM infused fibers. The processed fibers may be configured to concentrate oil therein increasing the OEM's exposure to the oil. The OEMs may remain in a dormant state in the OEM infused fibers until activated by water and exposed to the oil. In an example embodiment, the OEMs activate and multiply when exposed to water and then oil to digest the oil. The OEMs may then return to dormancy when the oil is exhausted defining an exposure and exhaustion cycle that may be repeatable. As such, the absorbent material may be reusable by cycling through multiple oil exposure and exhaustion cycles during which the OEMs are correspondingly activated and returned to dormancy. In an example embodiment, the OEM infused fibers are integrated into one or more of a loose absorbent material, a wipe, a rag, a towel, a pillow or a boom.

Example embodiments may provide for the generation of absorbent materials that have exceptional characteristics relative to their properties for absorption of oil or other petroleum products. However, example embodiments may further generate such materials so that they are reusable by virtue of their ability to perform multiple exposure and exhaustion cycles where OEMs are dormant until activated by water and exposed to oil, activate to digest the oil and then return to dormancy when the oil is exhausted. Moreover, example embodiments accomplish this without themselves providing any harmful impact on the environment.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. An absorbent material comprising:
banana tree stalk fibers separated and processed for moisture content reduction to generate processed fibers; and
oil eating microorganisms (OEMs) infused into the processed fibers to form OEM infused fibers, the OEMs remaining in a dormant state in the OEM infused fibers until activated by water and exposed to oil, wherein the processed fibers absorb the oil, and wherein the activated OEMs digest the oil.

2. The absorbent material of claim 1, wherein the OEMs are activated by water and multiply when exposed to the oil to digest the oil.

3. The absorbent material of claim 2, wherein the OEMs return to dormancy when the oil is exhausted.

4. The absorbent material of claim 1, wherein the absorbent material is reusable by cycling through multiple oil exposure and exhaustion cycles during which the OEMs are correspondingly activated and returned to dormancy.

5. The absorbent material of claim 1, wherein the OEM infused fibers are integrated into one or more of a loose absorbent material, a wipe, a rag, a towel, a pillow or a boom.

6. The absorbent material of claim 1, wherein the processed fibers are dried using one or more of heat, airflow and kinetic energy application methods.

* * * * *